(12) United States Patent
Divi et al.

(10) Patent No.: US 9,512,063 B2
(45) Date of Patent: Dec. 6, 2016

(54) PROCESS FOR THE PREPARATION OF ADVANTAME

(71) Applicant: Divi's Laboratories Limited, Ameerpet, Hyderabad (IN)

(72) Inventors: Murali Krishna Prasad Divi, Hyderabad (IN); Mysore Aswatha Narayana Rao, Hyderabad (IN); Shaik Nowshuddin, Hyderabad (IN)

(73) Assignee: Divi's Laboratories Limited (IN)

( * ) Notice: Subject to any disclaimer, the term of this patent is extended or adjusted under 35 U.S.C. 154(b) by 0 days.

(21) Appl. No.: 14/848,533

(22) Filed: Sep. 9, 2015

(65) Prior Publication Data

US 2016/0304439 A1   Oct. 20, 2016

(30) Foreign Application Priority Data

Apr. 20, 2015   (IN) .......................... 2019/CHE/2015

(51) Int. Cl.
```
C07C 231/12   (2006.01)
C07K 5/075    (2006.01)
C07C 45/45    (2006.01)
```
(52) U.S. Cl.
CPC ............ *C07C 231/12* (2013.01); *C07C 45/45* (2013.01); *C07K 5/0613* (2013.01)

(58) Field of Classification Search
CPC .................................................. C07K 5/0613
See application file for complete search history.

(56) References Cited

U.S. PATENT DOCUMENTS

| 5,480,668 A * | 1/1996 | Nofre ..................... A23L 1/2362 |
| | | 426/548 |
| 6,548,096 B1 | 4/2003 | Amino et al. |
| 6,794,531 B2 | 9/2004 | Nagashima et al. |
| 6,841,183 B2 * | 1/2005 | Nagashima .......... C07D 311/20 |
| | | 426/548 |
| 7,141,263 B2 | 11/2006 | Mori et al. |
| 7,238,830 B2 * | 7/2007 | Amino ..................... A23L 27/32 |
| | | 420/548 |

OTHER PUBLICATIONS

Stephen F. Martin, Synthesis of Aldehydes, Ketones, and Carboxylic Acids from Lower Carbonyl Compounds by C-C Coupling Reactions, Synthesis of Aldehydes, Ketones, and Carboxylic Acids from Lower Carbonyl Compounds, p. 635—Sep. 1979.
Mahata, et al., Formation of Acetaldehyde Enolate from Vinyl Acetate and its Reaction with Aromatic and Heterocyclic Aldehydes, an Efficient Synthesis of Enals and Polyenals, Synlett 2000, No. 9, 1345-1347, Received, Jun. 25, 2000.
Wittig, et al., New Methods of Preparative Organic Chemistry VI, Angew. Chem. internat. Edit., vol. 7 (1968) No. 1, pp. 7-14.
Kim et al., One-Step Synthesis of ortho-Hydroxycinnamaldehyde, Synthetic communications, vol. 34, No. 7, pp. 1223-1228, 2004.

* cited by examiner

*Primary Examiner* — Yate K Cutliff
(74) *Attorney, Agent, or Firm* — Caesar Rivise, PC

(57) ABSTRACT

A novel process for the preparation of N—[N-[3-(3-hydroxy-4-methoxyphenyl)-propyl]-L-α-aspartyl]-L-phenylalanine-1-methyl ester is described. It comprises, reacting isovanillin or its derivative with vinyl acetate followed by reductive condensation with L-[α-aspartyl]-L-phenylalanine-1-methyl ester.

4 Claims, No Drawings

PROCESS FOR THE PREPARATION OF ADVANTAME

FIELD OF INVENTION

The present invention relates to an improved process for the preparation of N—[N-[3-(3-hydroxy-4-methoxyphenyl)propyl]-L-α-aspartyl]-L-phenylalanine-1-methyl ester, known as Advantame, a non-caloric sweetener.

BACKGROUND OF THE INVENTION

Advantame is a novel sweetener developed by Ajinomoto Co. It is a derivative of Aspartame, chemically N—[N-[3-(3-hydroxy-4-methoxyphenyl)propyl]-L-α-[aspartyl]-L-phenylalanine-1-methyl ester, having the following structure:

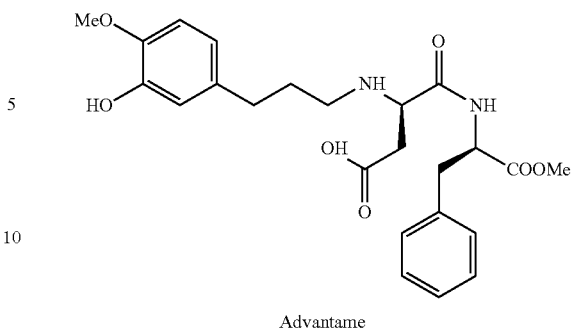

Advantame

The U.S. Pat. No. 6,794,531 B2, assigned to Ajinomoto Co., describes a process for the preparation of Advantame (Scheme 1), involving condensation of 3-(3-hydroxy-4-methoxyphenyl)-propionaldehyde (III) with Aspartame.

Scheme 1

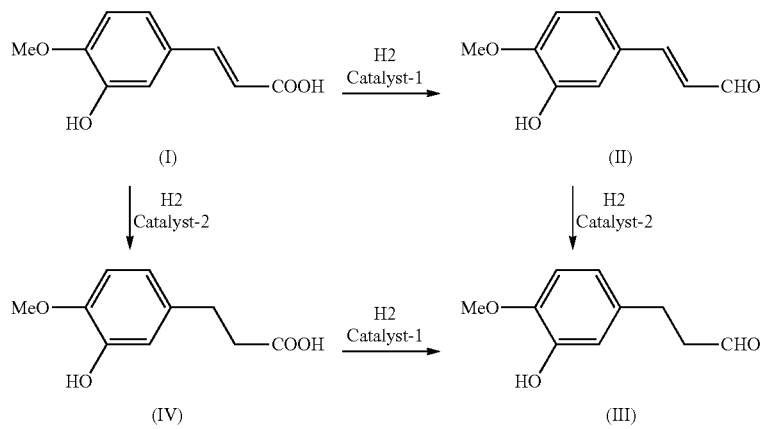

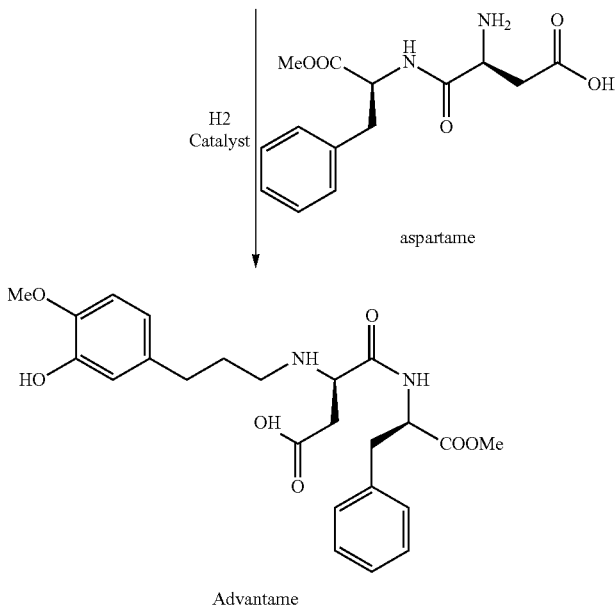

The required propionaldehyde derivative (III) was prepared by selectively reducing the corresponding cinnamic acid derivative (I) by hydrogenation using catalyst-1 consisting of palladium based catalyst, triaryl phosphine and pivalic acid anhydride to obtain corresponding cinnamaldehyde intermediate (II), followed by a second hydrogenation using catalyst-2, which can be any general catalyst based on palladium, platinum, nickel etc. Alternatively, (I) was first reduced by hydrogenation using catalyst-2 to obtain (IV) followed by reduction using catalyst-1. The propionaldehyde intermediate (III) was reductively aminated with aspartame to give advantame. Reduction of carboxylic acid of cinnamic acid intermediate to aldehyde using catalyst-1 was cumbersome. Ajinomoto reported a related process in its U.S. Pat. No. 6,548,096 B1 (Scheme 2):

Scheme 2

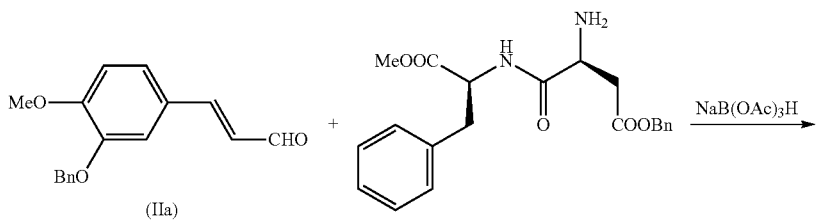

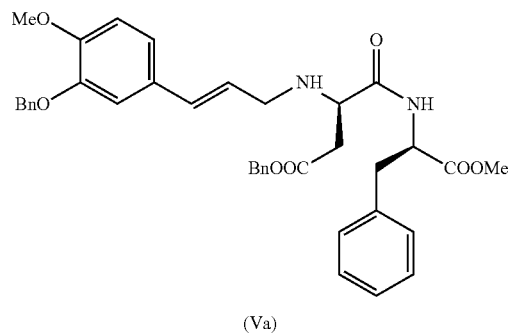

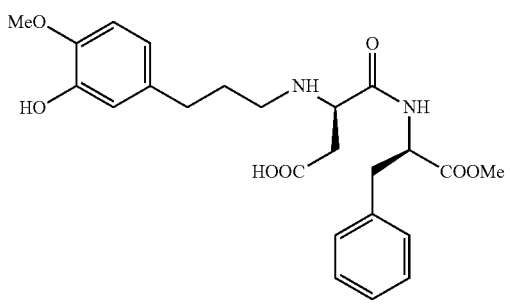

In this process, 4-methoxy-3-benzyloxy cinnamaldehyde (IIa) was condensed with benzyl protected aspartame by reductive amination using sodium triacetoxyborohydride to obtain (Va). Hydrogenation of (Va) using palladium catalyst resulted in deprotection of benzyl groups and saturation of the double bond to give Advantame. This process requires protection and later deprotection of both phenolic group of the cinnamaldehyde and carboxylic acid of aspartame through benzylation, which increases the number of steps and cost of the process. Ajinomoto described another process in U.S. Pat. No. 7,141,263 B2 (Scheme 3):

self-condensation of acetaldehyde enolate with unreacted aldehyde resulting in undesirable products and side reactions (Angew. Chem. Int. Ed. Engl. 1968, 7, 7-14; Synthesis 1979, 633-665). The Ajinomoto process (Scheme-3) also suffers for similar reasons. The process attempts to overcome this problem by slow addition of acetaldehyde to the alkaline solution of isovanillin. But the addition is excruciatingly slow taking about 45 hours (up to 96 hours as per Claim-6) making the process duration very long.

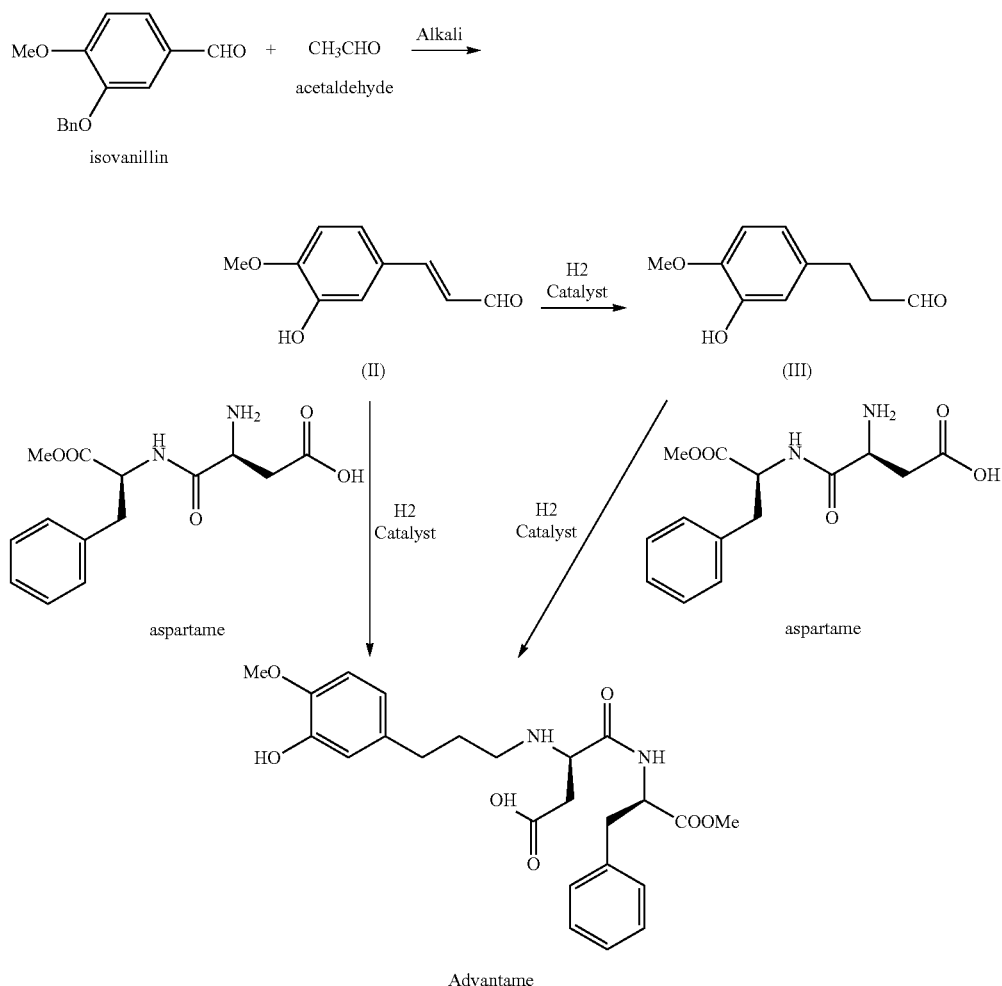

In the scheme-3, the first step is cross aldol condensation of isovanillin with acetaldehyde in the presence of an alkali to obtain (3-hydroxy-4-methoxy) cinnamaldehyde (II). Catalytic hydrogenation of (II) gives (III) which on reductive amination with aspartame gives Advantame. Direct reductive condensation of (II) with aspartame also results in Advantame. By this process (II) is obtained in much purer form compared to other processes where the corresponding cinnamic acid derivative is reduced to obtain intermediate (II) (Scheme 1). However, Scheme-3 process suffers from a major drawback. Cross aldol condensation between acetaldehyde and other carbonyl compound in an alkaline medium generally gives poor yields. This is mainly because of Because of the enumerated drawbacks of the above mentioned processes, there is thus a need for developing an improved process.

SUMMARY OF THE INVENTION

Since acetaldehyde enolate generated from acetaldehyde in the alkaline medium during aldol condensation results in a number of side reactions, it was hypothesized that generating acetaldehyde enolate from a non-aldehyde compound may be able to suppress side reactions during the aldol reaction. Indeed, such was found to be the case when vinyl acetate was used as a non-aldehyde compound to generate acetaldehyde enolate. The acetaldehyde enolate obtained from vinyl acetate on condensing with isovanillin resulted in highly pure (4-methoxy-3-hydroxy) cinnamaldehyde with good yields.

The present invention describes a novel process for Advantame based on vinyl acetate condensation with isovanillin or O-benzylisovanillin followed by reductive amination with Aspartame (Scheme-4):

I. Condensing isovanillin or its O-benzyl derivative with vinyl acetate in the presence of an alkali to obtain cinnamaldehyde derivative (II) or (IIa),
II. condensing (II) or (IIa) with aspartame through reductive amination using sodium borohydride and acetic acid to obtain (V) or (Vb),
III. catalytic hydrogenation of (V) or (Vb) to obtain Advantame.

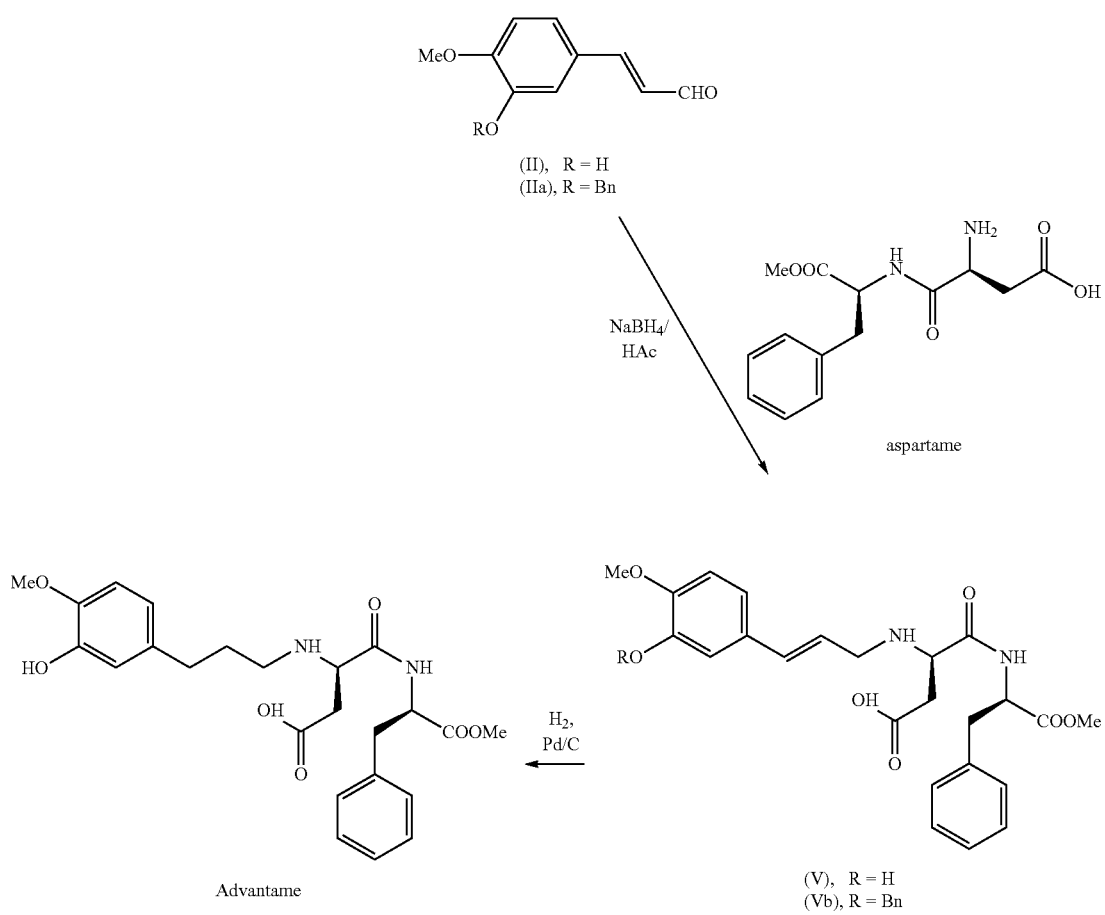

DETAILED DESCRIPTION OF THE INVENTION

The present invention describes a process (Scheme 4) for the preparation of Advantame which comprises:

Junjappa et al (Synlett. 2000, 9, 1345-1347) reported the preparation of cinnamaldehyde by refluxing a tetrahydrofuran solution of benzaldehyde and vinyl acetate using barium hydroxide as a base. Isolation involved diluting the reaction mixture with water and extraction with chloroform followed by column chromatography for purification. No hydroxyl substituted benzaldehyde was attempted, although other substituted aldehydes were studied. When 2.5 equivalents of vinyl acetate were used, a dienal (VI) was obtained in 61%.

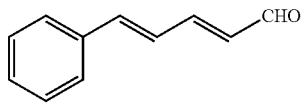

(VI)

Our initial attempts to prepare (3-hydroxy-4-methoxy) cinnamaldehyde by the method described by Junjappa et al resulted only in the acetylation of the phenolic group. (Scheme-5):

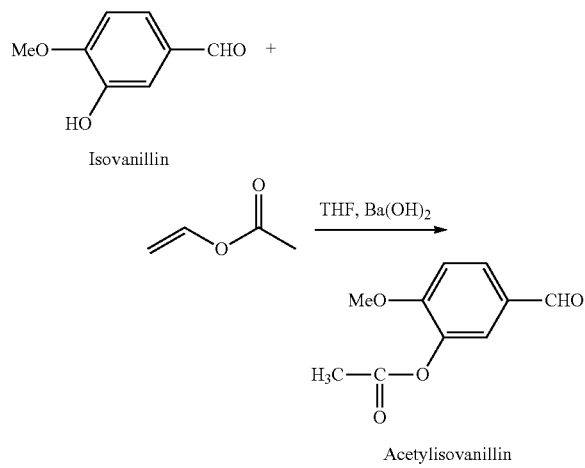

Scheme-5

Isovanillin

Acetylisovanillin

Change of solvents (acetonitrile, ethanol, methanol, etc) and bases (NaOH, KOH, Et$_3$N etc), did not improve the situation. Hence the phenolic group was protected with benzyl and the resulting O-benzylisovanillin was reacted with vinyl acetate. No reaction was observed at low or room temperature but significant amount of (IIa) was obtained when a solution of O-benzylisovanillin and vinyl acetate in methanol were autoclaved at 80° C. for 12 hours in presence of sodium carbonate. From the reaction mixture the product (IIa) was isolated through column chromatography in about 40% yield. The compound (IIa) was condensed with aspartame through reductive amination using sodium borohydride and acetic acid and the crude solid obtained was recrystallized from n-hexanes to get pure (Vb) in 78% yield (96% HPLC). Hydrogenation of (Vb) over Pd/C in methanol-water resulted in crude Advantame, which on crystallization from methanol gave pure Advantame in 55% yield (99.6% HPLC).

Although Advantame was obtained in good purity, the yields were poor at the first and final stages. Furthermore, the process involved an additional step of protecting isovanillin through benzylation.

Kown et al (Synthetic Communications, 2004, 34, 1223-1228) reported the preparation of 2-hydroxycinnamaldehyde using the method of Junjappa et al. From 2-hydroxybenzaldehyde and vinyl acetate in acetonitrile as solvent using potassium carbonate as the base they obtained 2-hydroxy cinnamaldehyde in 34% yield together with trace amounts of coumarin (Scheme-6):

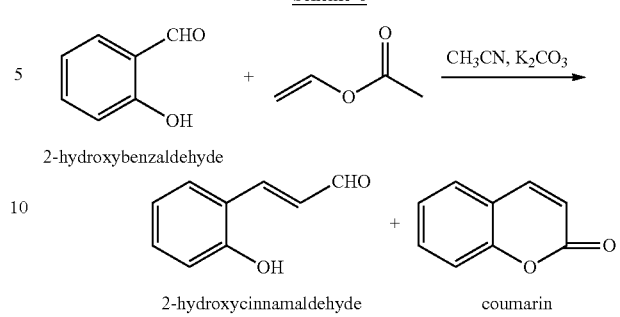

Scheme-6

2-hydroxybenzaldehyde 2-hydroxycinnamaldehyde       coumarin

Surprisingly no reaction was observed when Ba(OH)$_2$ or t-BuOK was used as the base. With 3-hydroxybenzaldehyde, corresponding cinnamaldehyde was obtained in about 43% yields. With 4-hydroxy benzaldehyde no reaction was observed. The fact that hydroxyl cinnamaldehyde can be obtained without protecting the phenolic group prompted us to explore further the reaction of isovanillin with vinyl acetate.

Systematic and detailed studies of the reaction conditions such as base, solvent, temperature and duration of reaction resulted in optimized reaction conditions where (II) was obtained in high yield and purity (>95% yield, >99.5% HPLC).

Best results were obtained when vinyl acetate was used in three equivalents to isovanillin and the reaction was conducted in water as solvent at −10±2° C. with 10 equivalent sodium hydroxide as the base. Formation of impurities was high at room temperature. When sodium hydroxide was used in 3 to 6 equivalents, the reaction was incomplete. Similarly, three equivalents of vinyl acetate were required for optimum results. It is interesting to note that no dienal similar to (IV) was formed as reported by Junjappa et al at 2.5 equivalents of vinyl acetate.

Condensation of (II) with aspartame was carried out by reductive amination using sodium borohydride in acetic acid at room temperature. Acetic acid acted both as a reagent and solvent. After the reaction, about 2 hours, the reaction mixture was diluted with water and extracted with ethyl acetate. Removal of the solvent and recrystallization of the residue with methyl t-butyl ether resulted in the compound (V) in 85% yield (>96% HPLC).

The compound (V) was hydrogenated using palladium/carbon catalyst in a mixture of methanol and water. After removal of the solvent, the residue was dissolved in water and extracted with n-butanol. Concentration of the solution and recrystallization from methanol-water mixture resulted in pure Advantame in 72% yield with 99.7% HPLC purity.

The embodiments of the present invention are further described in the following examples, which are not intended in any way to limit the scope of the invention.

Example-1

Preparation of O-Benzyl Isovanillin

Isovanillin (100 g, 0.657 mole) was dissolved in 600 mL water containing potassium hydroxide (47.9 g, 0.8553 mole). Benzyl chloride (109.6 g, 0.857 mole) was added drop wise at 10±2° C. for 25-30 min. After the addition, the reaction mixture was warmed to room temperature and refluxed for 12 h. After cooling, the aqueous layer was extracted with dichloromethane (3×100 mL). After drying the organic layer over Na$_2$SO$_4$, solvent was distilled at 40° C. to get brown thick liquid. It was recrystallized from ethanol to obtain O-benzylisovanillin (Yield: 122.2 g, 76.7%, 98.5% HPLC).

Example-2

Preparation of (3-benzyloxy-4-methoxyphenyl)cinnamaldehyde (IIa)

Benzyl isovanillin (50 g, 0.206 mole) was dissolved in 300 mL methanol in an autoclave SS flask. Sodium carbonate (21.87 g, 0.20 mole) and vinyl acetate (26.6 g, 0.3096 mole) were added to the flask and sealed. The flask temperature was maintained at 80° C. for 12 hour. After cooling, the content of the flask was collected and the solvent was removed under vacuum to get crude material. It was dissolved in ethyl acetate and washed with water (2×100 mL). The ethyl acetate layer was dried over Na$_2$SO$_4$ and the solvent was removed under vacuum at 50° C. to get brown crude product. It was purified using silica gel column by eluting with a mixture of hexanes and ethyl acetate (7:3 ratio) to obtain (3-benzyloxy-4-methoxyphenyl) cinnamaldehyde, (Yield: 22.2 g 40.1%).

Example-3

Synthesis of N—[N-[3-(3-benzyloxy-4-methoxyphenyl)propenyl]-L-aspartyl]-L-phenylalanine-1-methyl ester (Vb)

Sodium borohydride (2.4 g, 0.0634 mole) was added to acetic acid (28 g, 0.465 mole) and stirred at 10±2° C. After about 20 min, the reaction mass turned to a white suspension. To this was added (3-benzyloxy-4 methoxyphenyl) cinnamaldehyde (5.0 g, 0.0186 mole) and aspartame (5.4 g, 0.0183 mole) lot wise for 15-20 min at 10±2° C. and stirred for 2 hours. Water (50 mL) and ethyl acetate (75 mL), were added. The ethyl acetate layer was separated and washed with saturated sodium bicarbonate solution. After drying the ethyl acetate layer over Na$_2$SO$_4$, solvent was distilled under vacuum at 50° C. to get crude material. Crystallization using n-hexanes resulted in a yellow solid (Yield: 7.94 g, 78%, 96% HPLC)

Example-4

Preparation of Advantame

The compound obtained from Example-3 (3.0 g, 0.0054 mole) was dissolved in a solution containing methanol (30 mL) and water (20 mL). Palladium/carbon catalyst (0.1 g of 10%) added and the reaction mixture hydrogenated for 12 hours at about 50 psi pressure. After the reaction, the catalyst was filtered and the reaction mass distilled at 50° C. to give oily crude material. Crystallization in methanol and water gives off white solid of Advantame (Yield: 1.46 g, 55.8%, HPLC 99.6%).

Example-5

Synthesis of (3-hydroxy-4-methoxy) cinnamaldehyde (II)

Isovanillin (25 g, 0.164 mole) and sodium hydroxide (65.7 g, 1.6425 mole) were dissolved in 400 mL water and the solution was cooled to −10±5° C. To the solution was added vinyl acetate (14.2 g, 0.16 mole) drop wise over a period of 30 min and maintained for 12 hours. A second lot of vinyl acetate (14.2 g, 0.16 mole) was added and stirred for 6 hours and a third lot was added and stirred for 6 hours. The pH was adjusted to 2.0 with conc.HCl. The yellow solid obtained was filtered and recrystallized using ethanol to obtain (4-methoxy-3-hydroxy) cinnamaldehyde in pure form (Yield: 26.2 g, 90.1%, 99.6% HPLC).

Example-6

Synthesis of Advantame

Sodium borohydride (1.0 g, 0.02643 mole) was dissolved in 15 mL acetic acid and the solution was cooled to 10±2° C. After 20 min, the solution turned to a white suspension. To this suspension was added 4-methoxy-3-hydroxy) cinnamaldehyde (5.0 g, 0.02805 mole) and aspartame (7.5 g, 0.254 mole), allowed to cool to room temperature and stirred for 2 hours. The content was transferred to a hydrogenation flask and ethanol (30 mL), water (20 mL) and 5% palladium/carbon catalyst (0.5 g) were added. Hydrogenation was carried out for 10 hour at about 50 psi. The catalyst was filtered and the solvent removed under vacuum at 50±5° C. The crude oil obtained was dissolved in water and washed with toluene to remove impurities. The aqueous solution was extracted with n-butanol (3×25 mL). The butanol layers were pooled and concentrated under vacuum at 50±5° C. to get oily crude material. It was recrystallized using methanol-water mixture to obtain advantame in pure form (Yield: 8.82 g, 66%, 99.7% HPLC).

Example-7

Synthesis of N—[N-[3-(3-hydroxy-4-methoxyphenyl)propenyl]-L-aspartyl]-L-phenylalanine-1-methyl ester (V)

Sodium borohydride (1.0 g, 0.02643 mole) was added to 15 mL acetic acid and stirred at 10±2° C. After about 20 min, the reaction mass turned to a white suspension. To this were added (3-benzyloxy-4-methoxyphenyl) cinnamaldehyde (5.0 g, 0.0186 mole) and aspartame (7.5 g, 0.0255 mole). The reaction mixture was warmed to room temperature and stirred for 2 hours. Water (50 mL) was added and extracted with ethyl acetate (75 mL). The ethyl acetate layer was separated and washed with saturated sodium bicarbonate solution. After drying the ethyl acetate layer over Na$_2$SO$_4$, solvent was distilled under vacuum at 50° C. to get crude material. Crystallization using methyl tert-butyl ether resulted in pure solid of N—[N-[3-(3-hydroxy-4-methoxyphenyl) propenyl]-L-aspartyl]-L-phenylalanine-1-methyl ester (Yield: 21.0 g, 85%, 96.5% HPLC).

Example-8

Synthesis of Advantame

N—[N-[3-(3-hydroxy-4-methoxyphenyl)propenyl]-L-aspartyl]-L-phenylalanine-1-methyl ester from Example-7 (20.0 g, 0.0438 mole) was dissolved in a mixture of methanol (100 mL) and water (20 mL), transferred to a hydrogenation flask. To this was added 5% Palladium/carbon catalyst (0.5 g) and hydrogenated for 10 hours at about 50 psi pressure. The catalyst was filtered and the filtrate was concentrated at 50° C. under vacuum to get an oily crude compound. It was dissolved in water and washed with toluene to remove impurities. The aqueous phase was extracted with n-butanol. The n-butanol layer was concentrated at 50° C. under vacuum to get crude compound. It was recrystallized using methanol-water mixture to obtain Advantame (Yield: 15.1 g, 72%, 99.7% HPLC).

We claim:

1. A process for the preparation of N—[N-[3-(3-hydroxy-4-methoxyphenyl)-propyl]-α-aspartyl]-L-phenylalanine-1-methyl ester (Advantame) comprising:

condensing isovanillin or O-benzylisovanillin having the following structure:

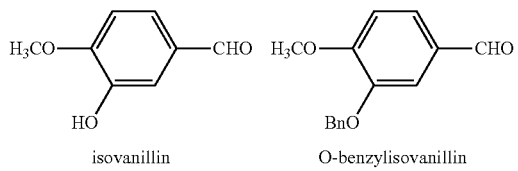 [SMILES: COc1ccc(C=O)cc1O ; COc1ccc(C=O)cc1OCc1ccccc1]

isovanillin      O-benzylisovanillin with vinyl acetate having the structure:

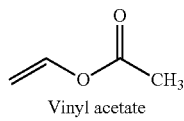

Vinyl acetate in aqueous alkaline medium to obtain (3-hydroxy-4-methoxy) cinnamaldehyde (II) or its derivative (IIa) having the structure:

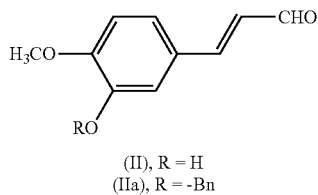

(II), R = H
(IIa), R = -Bn

Condensing (3-hydroxy-4-methoxy) cinnamaldehyde (II) or its derivative (IIa) with Aspartame having the structure:

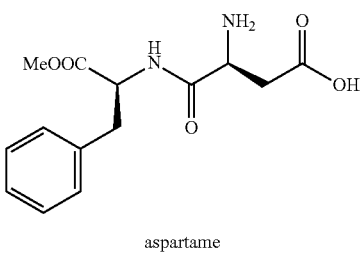 [SMILES: COC(=O)[C@H](Cc1ccccc1)NC(=O)[C@@H](N)CC(=O)O]

aspartame through reductive amination to obtain a phenylpropenyl derivative of Aspartame (V or Vb) having the structure:

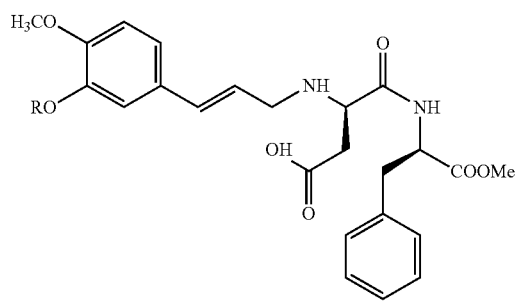

(V), R = H
(Vb), R = Bn and subjecting (V) or (Vb) to catalytic hydrogenation.

2. A process according to claim-1, wherein condensation of isovanillin or O-benzylisovanillin with vinyl acetate is carried out at a temperature range of −15° to 0° C.

3. A process according to claim-1, wherein condensing (4-methoxy-3-hydroxy)cinnamaldehyde (II) or its derivative (IIa) with Aspartame through reductive amination is carried out using sodium borohydride and acetic acid.

4. A process for the preparation of (3-hydroxy-4-methoxy) cinnamaldehyde (II) or its derivative (IIa) by condensing isovanillin or O-benzylisovanillin with vinyl acetate in aqueous alkaline medium.

* * * * *